US010729619B2

(12) United States Patent
Tsaur et al.

(10) Patent No.: US 10,729,619 B2
(45) Date of Patent: Aug. 4, 2020

(54) CAPSULE SEALING COMPOSITION AND ITS SEALING METHOD THEREOF

(71) Applicants: Garry Tsaur, Rowland Heights, CA (US); Frank Tsaur, Rowland Heights, CA (US); Ting-Hua Wang, Rowland Heights, CA (US)

(72) Inventors: Garry Tsaur, Rowland Heights, CA (US); Frank Tsaur, Rowland Heights, CA (US); Ting-Hua Wang, Rowland Heights, CA (US)

( * ) Notice: Subject to any disclaimer, the term of this patent is extended or adjusted under 35 U.S.C. 154(b) by 264 days.

(21) Appl. No.: 15/585,551

(22) Filed: May 3, 2017

(65) Prior Publication Data

US 2018/0318171 A1 Nov. 8, 2018

(51) Int. Cl.
*A61J 3/07* (2006.01)
*A61K 9/48* (2006.01)

(52) U.S. Cl.
CPC .................................... *A61J 3/072* (2013.01)

(58) Field of Classification Search
None
See application file for complete search history.

(56) References Cited

U.S. PATENT DOCUMENTS 4,893,721 A * 1/1990 Bodenmann ............ A61J 3/071 206/530
RE33,251 E * 7/1990 Wittwer .................. A61J 3/072 156/275.1
2001/0008637 A1* 7/2001 Hochrainer ............. A61J 3/071 424/451
2007/0184077 A1* 8/2007 Vanquickenborne ... A61J 3/072 424/400
2018/0325777 A1* 11/2018 Huysmans .............. A61J 3/072

* cited by examiner

*Primary Examiner* — Hemant Desai
*Assistant Examiner* — Tanzim Imam
(74) *Attorney, Agent, or Firm* — WPAT, PC

(57) ABSTRACT

Present invention relates to a capsule sealing composition and the method of using said composition for sealing capsules. Said sealing composition contains an acidic or alkaline solute and a volatile solvent; said sealing method uses the characteristics of capillary action ad volatile solvents to dissolve and seal the junction of the capsule cover and capsule body and said capsule then becomes a sealed capsule and the drugs contained in the capsule will not leak easily.

14 Claims, 2 Drawing Sheets

CAPSULE SEALING COMPOSITION AND ITS SEALING METHOD THEREOF

BACKGROUND OF THE INVENTION

Field of the Invention

Present invention relates to a capsule sealing composition and the method of using said composition for sealing capsules. In particular, the feature of said method is sealing capsules by using a volatile solvent and through capillary action.

Description of the Prior Art

Capsule is a pharmaceutical dosage form with a thickness between 0.07 mm and 0.7 mm under rapid development and has been widely used in drugs for oral administration such as pharmaceuticals and health food. Capsules have the advantages of easy storage, accurate dosage and controlled-release. Moreover, capsules can mask the bad smell of the active pharmaceutical ingredients of drugs and maintain pharmaceutical activity and therefore can be easily accepted by the recipients. The dosage form of a capsule can seal a drug inside a capsule and, due to its sealing feature, the drug sealed inside the capsule can maintain long-term stability by prevention of activity reduction caused by direct contact with outside air and moisture.

Commercially available capsules can be divided into hard capsules and soft capsules based on their appearance. The hard capsule is a two-piece combination, including the capsule body and capsule cover, but complete sealing of such capsules is not easy. To take into consideration the abovementioned features, liquid drugs usually are coated with soft capsules. The coating and filling processes during manufacturing of soft capsules are usually conducted simultaneously. To avoid rupture of the soft capsules during the process of manufacturing, the manufacturing process needs to be adjusted to increase the thickness of capsules. Yet, absorption after ingestion may be difficult if the capsule shell is too thick, or may even result in non-effectiveness or discomfort due to ineffective release of the content of a capsule. Hence, the purpose of consumer medicine and health can be better protected if a method for better sealing the hard capsules is available to replace the thickness issue of soft capsules.

The materials for making capsules include gelatin, sorbitol, hydroxypropyl methylcellulose (HPMC) and non-essential additives, such as non-transparent edible pigments, opacifier, glycerol or other additives, so as to reform or change the appearance or color of capsules.

The traditional material used to produce capsules is gelatin which is the protein or peptide extracted from animal skin, bones or connective tissues and contains collagen, and the hydrophilic light-yellow protein layer obtained after boiling is gelatin.

Another common material for making capsules is hydroxypropyl methylcellulose (HPMC) which is a viscous polymer and is usually used as an excipient, emulsifying agent, thickening agent, suspending agent or a replacement for gelatin in drugs for oral administration. After treated with an alkali, the hydroxyl group of cellulose is deprotonated and the generated alkoxy anion may be condensed with propylene oxide methyl to form hydroxypropyl cellulose ether; or alternatively, condensed with methyl chloride to form methyl cellulose ether. The two reactions occur simultaneously will generate hydroxypropyl methyl cellulose.

In addition, many other alternative materials are available for making capsules, including algae extract, i.e. the alternative material polysaccharide colloid. Plant materials can prevent crosslinking reaction between the animal proteins contained in the capsules and maintain the strength of the capsule body. Moreover, because of the recent incidents of the BSE epidemic reported in the U.S., improved soft capsules have gradually attracted more attention. Other alternative materials, such as agar gel, ether-soluble starch derivatives and HPMC, ie, carrageenan, also have gradually increased their market shares.

Hard capsules are composed of upper and lower shells, the upper shell is known as the capsule cover or cap and the lower shell is known as the capsule body and is prepared in advance before filling. When filling a capsule with its content, the capsule body and capsule cover are placed separately, and the capsule body is placed in a specific "hole" module with the opening facing up, the material to be filled is delivered through a transfer tube into the capsule body and appropriate pressure is applied to the capsule cover and capsule body to combine the two pieces and then the capsule-sealing procedure is complete.

Dry powder with low-water content such as starch, lactose or oily adjuvant is required when using the aforementioned method for packaging powder, solid particulates, drug solution or excipients, and such method is not suitable for coating water in the capsule because the capsule will dissolve and rupture when it is in contact with water and water can easily escape from the capsule shell.

As disclosed in the patent CN1182842C, certain active pharmaceutical ingredients need to be administered in the form of a compound carrier and among which 1,2-propanediol or isosorbide dimethyl ether is usually used as the solvent in the carrier medium. However, solvents such as 1,2-propanediol can easily migrate from the capsule and move into the capsule shell, resulting in dissolving of the capsule; moreover, the mixture of gelatin and 1,2-propanediol is highly viscous which is unnecessary.

As revealed in the patent U.S. Pat. No. 4,756,902A, the method for sealing the capsule shell may include applying alcohol to the junction of capsule cover and capsule body and heating the capsule to around 100° C. to keep a semi-dissolved state before coating the junction with a layer of gelatin. In addition, patent EP0152517B also discloses that applying alcohol and then heat to the capsule junction can melt the junction. However, the methods mentioned above also have drawbacks, such as easy deformation or shrinkage of the capsule shell due to moisture contained in the aqueous solution.

Due to the above limitations, use of alcohol (including ethanol, propanol, or propylene glycol) at the time of capsule packaging still has its shortcomings and the capsule sealing method needs to be modified; moreover, current method used for capsule sealing can easily cause capsule deformation or leakage of the capsule content, which increases the defects in capsule manufacturing as well as the production cost. Furthermore, to maintain the materials of the capsule shell, e.g. gelatin or HPMC, at a semi-dissolved state, applying heat or dissolving such materials in a low-concentration aqueous dissolution is required. According to the tests conducted by the inventor(s), to appropriately dissolve the capsule junction, trace amount of the solvent at the precise location is the key for complete sealing of the capsule shell without making any damage.

SUMMARY OF THE INVENTION

To solve the abovementioned issues of capsule deformation and content leakage occurred during the capsule sealing process due to the features of the sealing solvents, present invention provides a capsule sealing composition and its sealing method to improve the method for sealing capsules.

According to the invention, the capsule sealing method of the invention includes:

diluting solute(s) with a solvent to a concentration that does not cause any damage to the capsule;

gradually increasing the concentration of the solute in the solvent during the process of evaporation by taking the advantages of volatile solvents and capillary action, meanwhile, guiding the remaining solution to the top of the junction of capsule body and capsule cover through capillary action; and until evaporation is complete, the concentration of the solute in the solution is sufficient to locally dissolve the contact surface of the capsule and combine the capsule cover and capsule body into one piece.

According to the invention, the sealing composition of the invention comprises of a solute and a volatile solvent, said solute contains an acidic solution or an alkaline solution, and said solute can be replaced by water.

In one embodiment, the ratio of said solute and the volatile solvent is 1:1 to 1:15.

In the preferred embodiment, the preferred ratio of said solute and the volatile solvent is 1:4 to 1:6.

In one embodiment, said alkaline solution is an aqueous solution of metal oxides or alkaline earth metals, the alkaline metal oxide may be potassium hydroxide or sodium hydroxide, the concentration of the aforementioned solution is from 0.1 mole/L to a saturated solution.

In one embodiment, said acidic solution is an organic or inorganic acid solution, the organic acid is citric acid or acetic acid, and the inorganic acid is hydrochloric acid or sulfuric acid, the concentration of the aforementioned solution is from 0.1 mole/L to a saturated solution.

In one embodiment, the volatile solvent is methanol, ethanol, propanol, isopropanol, or butanol.

In one embodiment, the sealing composition may further contain gelatin, hydroxypropyl methyl cellulose, guar gum, or agar gel, and additives such as the pharmaceutically acceptable plasticizers and light blocking agent.

In one embodiment, the plasticizer is selected from the group consisting of the following: glycerin, sorbitol, maltose, glucose, polysaccharides, sucrose, xylitol, mannitol, 1,2-propylene glycol, and polyethylene glycol.

In one embodiment, the light blocking agent is selected from the group consisting of the following: caramel, titanium oxide, and iron oxide.

According to the invention, the capsule sealing method comprises the following steps:

combining the capsule cover and capsule body;

affixing the aforementioned sealing composition to one side or between the two sides of the inner side of the capsule cover and outer side of the capsule body;

the space between the inner side of the capsule cover and outer side of the capsule body is filled with the volatile solvent through capillary action and the solute concentration of the sealing compound increases with solvent evaporation until its concentration is sufficient to dissolve the contacted area of the capsule to seal the capsule;

the capsule is a sealed capsule.

In one embodiment, the filling of the capsules produced by this sealing method is a pharmaceutical composition or health food in the form of a liquid, suspension, paste, powder or granule.

DETAILED DESCRIPTION OF THE PREFERRED EMBODIMENT

Figure 1:
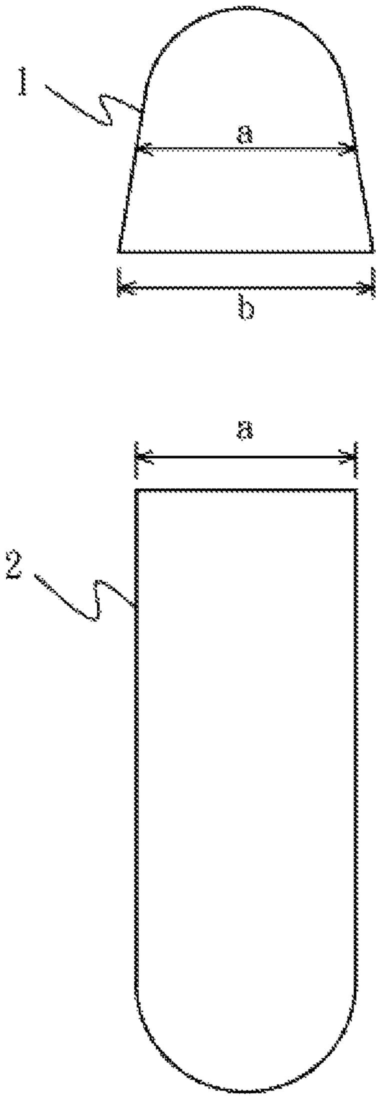
FIG. 1 shows the diagram of the capsule sealed by using the capsule sealing method of the invention.

All technical and scientific terms used in the invention, unless otherwise specified, have the common meanings that are understood by person skilled in the art. The foregoing detailed description of the invention and the specific examples are provided herein for the purpose of illustration only, and the invention is not limited to the preferred embodiments shown. It should be understood that any changes or modifications within the spirit of the invention shall be included in the scope of present invention.

Present invention provides a capsule sealing composition, said capsule sealing composition comprises of a solute and a carrier, said solute is an acidic solution or an alkaline solution, and said carrier is a volatile solvent.

Present invention also provides a capsule sealing method, said capsule sealing method refers to applying the aforementioned capsule sealing composition to the junction of the capsule cover and the capsule body and allowing the composition to infiltrate into the space between the capsule cover and the capsule body by capillary action so as to dissolve the capsule shell and form a sealing ring.

Regarding the aforementioned method, the size of the capsule is not restricted and the amount of the content is adjusted to between the range of 1 mg and 10 g.

Regarding the aforementioned method, the capillary action refers to the liquid is elevated inside a tiny space due to cohesion and adhesion and against the gravity.

The material of the capsule of present invention is a substance that retains the characteristic of reversible gelling after drying. Said substance is made of HPMC, gelatin, agar, starch, alginic acid or guar gum, and the preferred material for making the capsule is those that contain gelatin or HPMC and a plasticizer. In addition, the capsule material may also contain additives such as a light blocking agent, if required.

Regarding the aforementioned gelatin, which is obtained from collagen hydrolyzed and extracted from animals such as cows or pigs. Also, the aforementioned gelatin with the characteristic of reversible gelling is subjected to alkaline treatment, acidic treatment or chemical modification. Acid-treated gelatin refers to the gelatin that is hydrolyzed with hydrochloric acid or sulfuric acid; alkali-treated gelatin refers to the gelatin that is hydrolyzed with bases such as lime; chemically modified gelatin refers to the gelatin whose amino group is treated with organic acid, e.g. succinic acid or phthalic acid.

According to the invention, the aforementioned plasticizer may contain, but not limited to, glycerol, sorbitol, maltose, glucose, polysaccharides, sucrose, xylitol, mannitol, propylene glycol, polyethylene glycol and the like.

According to the invention, the aforementioned light blocking agent may contain, but not limited to, caramel, titanium oxide, iron oxide and the like.

The form of the capsule filling of present invention is not restricted and may be a liquid, suspension, paste, powder, granule and the like.

The thickness of the hard capsule of present invention is not restricted, but a thickness between 0.01-5 mm is preferred and the preferred thickness is 0.05-1 mm.

The capsule of present invention can be used in pharmaceuticals, quasi-pharmaceuticals, food, cosmetics and other purposes, according to the composition of the filling.

Regarding the aforementioned pharmaceuticals, quasi-pharmaceuticals, food, cosmetics, the pharmaceutical ingredient(s) of the capsule of present invention is not restricted, as long as the ingredient(s) does not damage the capsule's functions. The pharmaceuticals include but not limited to vitamins, antipyretics, analgesics, anti-inflammatory agents, anti-ulcer agents, cardiac stimulant, anti-coagulants, hemostatic agents, anti-resorptive agents, angiogenesis-inhibiting agents, antidepressants, anti-tumor agents, antitussive and expectorant agent, muscle relaxants, antiepileptic agents, antiallergic agent, arrhythmia therapeutic agents, vasodilators, antihypertensive diuretics, diabetes therapeutic agents, antituberculosis agents, hormonal agents, analgesics, antibacterial agents, antifungal agents and antiviral agents and the like, but is not limited to the abovementioned pharmacological effects and all of the pharmaceutical ingredients that have relatively poor water solubility are included as the subjects of the hard capsule of present invention. Substances with poor solubility are preferred.

The invention will now be described more specifically with reference to the schematic diagram of FIG. 1 to FIG. 4 by using the examples.

The appearance of the capsule used in present invention for sealing is shown in FIG. 1, but the appearance is not limited to the diagram shown. All capsules with an appearance that can be sealed by using the method of present invention are included in the invention.

Figure 2:
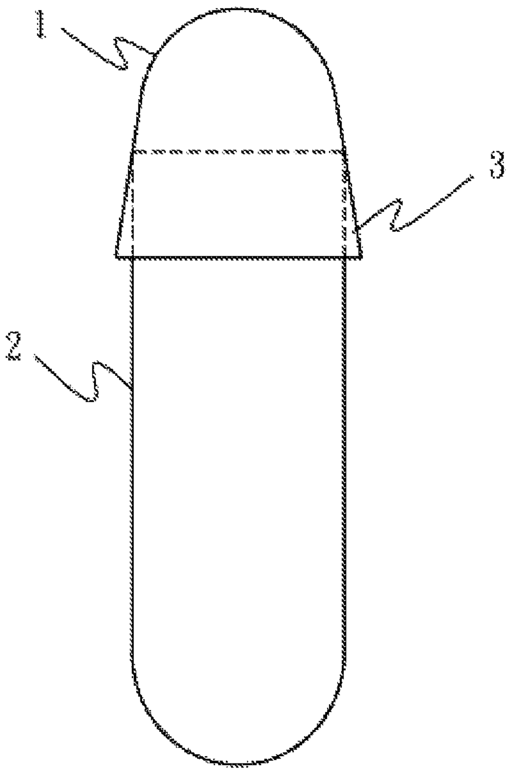
FIG. 2 shows another diagram of the capsule sealed by using the capsule sealing method of the invention.
Figure 3:
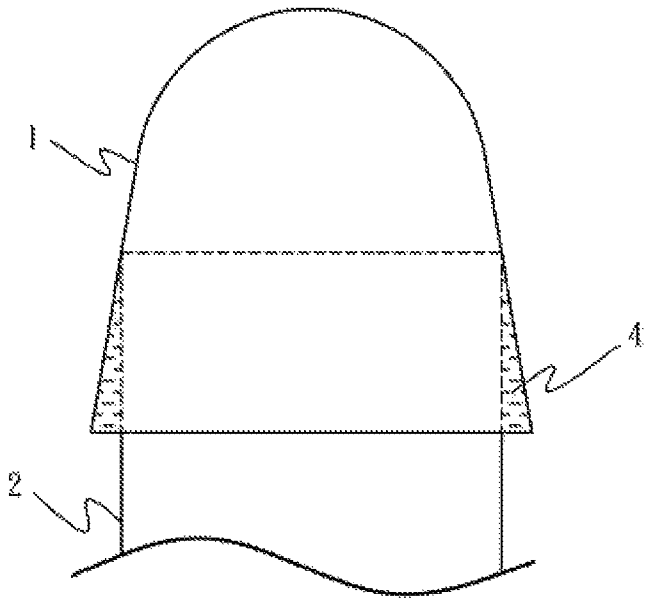
FIG. 3 shows the schematic diagram of the sealing composition of the capsule sealed by using the capsule sealing method of the invention.
Figure 4:
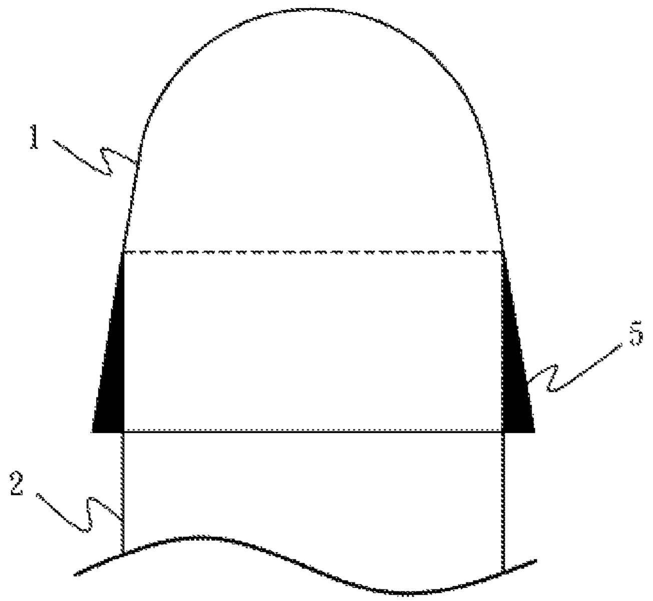
FIG. 4 shows the diagram of a sealed capsule produced by using the capsule sealing method of the invention.

The appearance of the capsule used in present invention for sealing is shown in FIG. 1, the outer diameter (b) of the capsule cover (1) needs to be larger than the outer diameter (a) of the capsule body (2), and the diameter (a) of the inner width of the capsule cover is similar to the outer diameter (a) of the capsule body (2), the combination of said capsule body (2) and the capsule cover (1) is shown in FIG. 2, the inner inside of the capsule cover (1) is not completely sealed with the capsule body (2) and a certain filling space (3) exists between the capsule body (2) and the capsule cover (1), said filling space (3) is an angle formed between the capsule body (2) and the capsule cover (1) and the filling space (3) is used for applying or injecting the sealing composition.

EXAMPLE 1

The capsule sealing composition provided in present invention is used for sealing the capsule, said composition comprises of a (A) solute and a (B) volatile solvent. The aforementioned solute may be an acidic solution, e.g. hydrochloric acid, citric acid, acetic acid, sulfuric acid and the like, or may be an alkaline solution, such as sodium hydroxide solution and potassium hydroxide solution and the like, the solute may be replaced by water; the aforementioned volatile solvent may be an alcohol, including methanol, ethanol, 1-propanol, 2-propanol, 1-butanol and the like. The ratio of the solute and the volatile solvent contained in the aforementioned composition is 1:1 to 1:15; the preferred ratio the solute and the volatile solvent contained in the aforementioned composition is 1:3 to 1:10; the preferred ratio the solute and the volatile solvent contained in the aforementioned composition is 1:4 to 1:6; in addition, the concentration of the aforementioned solute is 1 mole/L to a saturated solution. The aforementioned composition may contain gelatin and vegetable gum, such as hydroxypropyl methylcellulose (HPMC), guar gum, or agar gel.

After the capsule cover (1) is fitted with the capsule body (2) (FIG. 2), a filling space (3) is generated, said filling space is between the capsule cover (1) and the capsule body (2), and the sealing composition (4) can be affixed to the overlapping space (FIG. 3) of the inner side of the capsule cover (1) and the outer side of the capsule body (2), the sealing composition (4) is attached to the capsule and the sealed composition (4) can carry the affixed sealing composition (4) to the conjunction of the capsule cover (1) and capsule body (2) on the capsule surface through its capillary action, that is, the region where the capsule cover (1) with the inner diameter of a contacts the outer area of the capsule body with the diameter of a so as to allow the sealing composition (4) stay in the original filling space (3). Moreover, because the sealing composition (4) contains a volatile solvent, said solvent will evaporate from the opening side over time and because the amount of the solvent will decrease while the amount of solute remains the same, the concentration of solute will increase gradually. After the concentration of solute is increased to a certain level that is sufficient to dissolve the contacted capsule surface, a fusion section (5) is formed at the original filling space (3).

After formation of the fusion section (5), the capsule can be sealed. In addition, because only trace amount of solute is left, the sealing composition (4) can be elevated to the top of the filling space (3) through capillary action.

Meanwhile, because only trace amount of the sealing composition (4) is present, the capsule shell of the filling space (3) can be dissolved without deformation which may cause leakage of the drug contained in the capsule and entry of outside air can be blocked to prevent deterioration of the drug due to air exposure.

The foregoing detailed description of the invention and the specific examples are provided herein for the purpose of illustration only, and the invention is not limited to the preferred embodiments shown. It should be understood that any changes or modifications within the spirit of the invention shall be included in the scope of present invention.

In summary, present invention not only provides a novel method, but also discloses a number of improved features of technologies as described above. Therefore, the invention meet the requirements of novelty as well as non-obviousness.

What is claimed is:

1. A capsule sealing method, comprising:

dilution of a solute with a volatile solvent to a concentration that does not melt a capsule;

then gradually increasing the concentration of the solute in the solvent during a process of evaporation by taking advantage of a volatility of the solvent and capillary action, meanwhile, guiding a remaining solution of the solute and the solvent to a top of an angle formed between a capsule body and a capsule cover through capillary action;

wherein until evaporation is complete, the concentration of the solute in the solution is sufficient to locally melt a contact surface of the capsule and combine the capsule cover and the capsule body into one piece; and wherein the solute is acidic aqueous solution or alkaline aqueous solution.

2. The capsule sealing method as recited in claim 1, wherein a ratio of the solute and the volatile solvent is between 1:1 and 1:15.

3. The capsule sealing method as recited in claim 2, wherein the ratio of the solute and the volatile solvent is between 1:4 and 1:6.

4. The capsule sealing method as recited in claim 1, wherein the alkaline aqueous solution is an aqueous solution of a metal oxide or alkaline earth metals.

5. The capsule sealing method as recited in claim 4, wherein a metal oxide is potassium hydroxide or sodium hydroxide.

6. The capsule sealing method as recited in claim 4, wherein the concentration of the alkaline aqueous solution is 1 mole/L to a saturation solution.

7. The capsule sealing method as recited in claim 1, wherein the acidic aqueous solution is an aqueous solution of an organic acid or an inorganic acid.

8. The capsule sealing method as recited in claim 7, wherein the aqueous solution of the organic acid is citric acid or acetic acid.

9. The capsule sealing method as recited in claim 7, wherein the aqueous solution of the inorganic acid is hydrochloric acid or sulfuric acid.

10. The capsule sealing method as recited in claim 7, wherein the concentration of the acidic aqueous solution is 1 mole/L to a saturation solution.

11. The capsule sealing method as recited in claim 1, wherein the volatile solvent is methanol, ethanol, 1-propanol, 2-propanol or 1-butanol.

12. The capsule sealing method as recited in claim 1, wherein the solution further contains gelatin, hydroxypropyl methyl cellulose, guar gum, or agar gel, a pharmaceutically acceptable plasticizer and a light blocking agent.

13. The capsule sealing method as recited in claim 12, wherein the plasticizer is selected from the group consisting of the following: glycerin, sorbitol, maltose, glucose, polysaccharides, sucrose, xylitol, mannitol, 1,2-propylene glycol, and polyethylene glycol.

14. The capsule sealing method as recited in claim 12, wherein the light blocking agent is selected from the group consisting of the following: caramel, titanium oxide, and iron oxide.

* * * * *